United States Patent
Küçük et al.

(10) Patent No.: US 10,098,812 B2
(45) Date of Patent: Oct. 16, 2018

(54) MULTI-COMPONENT CONTAINER

(71) Applicant: SCHOTT Schweiz AG, St. Gallen (CH)

(72) Inventors: Mustafa Küçük, Staad (CH); Klaus Bamberg, Zuchwil (CH); Bernd Hoppe, Ingelheim (DE)

(73) Assignee: SCHOTT SCHWEIZ AG, St. Gallen (CH)

( * ) Notice: Subject to any disclaimer, the term of this patent is extended or adjusted under 35 U.S.C. 154(b) by 211 days.

(21) Appl. No.: 14/735,058

(22) Filed: Jun. 9, 2015

(65) Prior Publication Data
US 2015/0352008 A1    Dec. 10, 2015

(30) Foreign Application Priority Data
Jun. 10, 2014    (DE) .......................... 10 2014 211 018

(51) Int. Cl.
*A61M 5/31*    (2006.01)
*A61J 1/00*    (2006.01)

(52) U.S. Cl.
CPC .............. *A61J 1/00* (2013.01); *A61M 5/3129* (2013.01); *A61M 5/3134* (2013.01); *A61M 5/3135* (2013.01); *A61M 2005/3139* (2013.01)

(58) Field of Classification Search
CPC .......... A61J 1/2048; A61J 1/1487; A61J 1/00; A61M 2005/3139; A61M 2005/3132; A61M 5/3129; A61M 5/3135; A61M 5/50; A61M 5/3134; A61L 31/14
See application file for complete search history.

(56) References Cited

U.S. PATENT DOCUMENTS

| | | | | |
|---|---|---|---|---|
| 3,885,297 A | * | 5/1975 | Tischlinger | A61M 5/3129 222/323 |
| 5,328,484 A | * | 7/1994 | Somers | A61M 5/3202 604/110 |
| 5,782,815 A | * | 7/1998 | Yanai | A61J 1/062 222/386 |
| 6,544,233 B1 | * | 4/2003 | Fukui | A61M 5/31596 604/191 |
| 2002/0045865 A1 | * | 4/2002 | Mitomi | A61M 5/3134 604/207 |
| 2010/0280414 A1 | | 11/2010 | Haywood et al. | |

FOREIGN PATENT DOCUMENTS

DE    10102054 A1    8/2002

* cited by examiner

*Primary Examiner* — Deanna K Hall
(74) *Attorney, Agent, or Firm* — Ohlandt, Greeley, Ruggiero & Perle, L.L.P.

(57) ABSTRACT

A container for storing and/or applying a substance is provided. The container includes a glass body having a substantially hollow cylindrical shape and enclosing a cavity, as well as a distal end with a first opening and a proximal end with a second opening. One or more connecting elements are attached to the glass body at the distal end and are made of a plastic material. The plastic material is a thermoplastic or thermosetting plastic material and the glass body and the or each connecting element are connected to each other by use of a joint. The connecting element arranged at the distal end includes a passage channel communicating with the first opening. The first and second openings are enclosed by end faces and immediately adjacent surfaces of the glass body and the connecting element(s) is/are attached to the glass body via the end faces and the immediately adjacent surfaces.

16 Claims, 1 Drawing Sheet

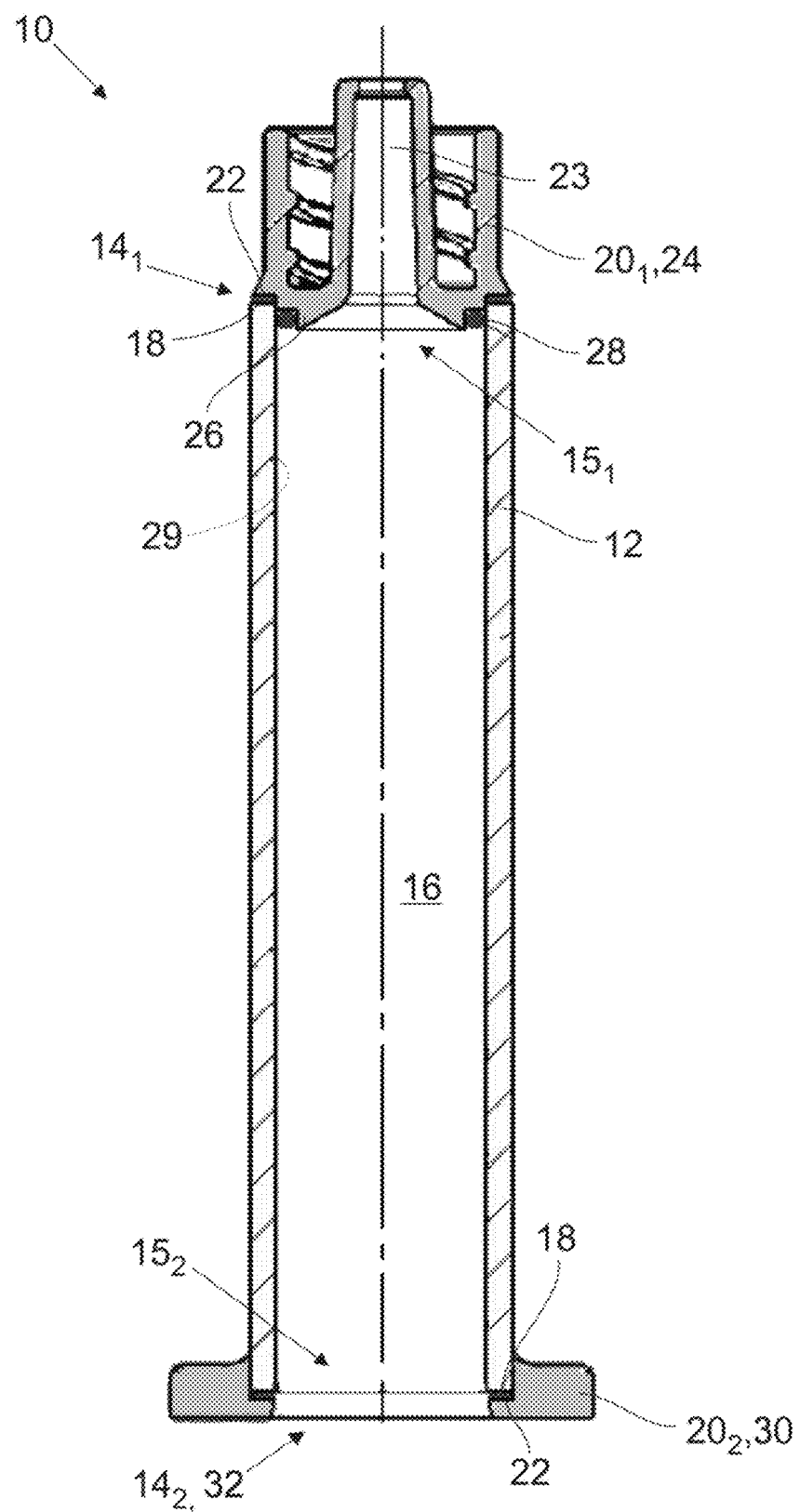

MULTI-COMPONENT CONTAINER

CROSS REFERENCE TO RELATED APPLICATIONS

This application claims benefit under 35 U.S.C. § 119(a) of German Patent Application No. 10 2014 211 018.1 filed Jun. 10, 2014, the entire contents of which are incorporated herein by reference.

BACKGROUND

1. Field of the Disclosure

The present invention relates to a container for storing and/or applying a substance, comprising a glass body enclosing a cavity and having a distal end with a first opening, and one or more connecting elements which are attached to the glass body and are made of or comprise a plastic material, wherein one of the connecting elements is disposed at the distal end. As an example of substances that can be stored in the container according to the invention pasty, liquid as well as gaseous substances and mixtures and dispersions and emulsions may be mentioned. Since glass is highly inert against a majority of common chemicals and pharmaceutical substances and has a high diffusion resistance, it is particularly suitable for storing pharmaceutical substances. Due to the high diffusion resistance permeation losses during storage are low, which is in particular an essential aspect for high-quality pharmaceutical substances.

2. Description of Related Art

Particularly in modern pharmaceutical substances that are very expensive, highly effective and very sensitive, there is a growing tendency to use pre-filled syringes or carpules, wherein for the reasons mentioned above glass syringes are suited. With pre-filled syringes it is no longer necessary to transfer the substance from one container into another container. Rather, the pre-filled syringe is ready for use immediately after unpacking. Apart from saving time for the doctor or the nurse there is an additional advantage in that losses are avoided that frequently occur during the transfer from one container to the other. In addition, during the transfer there is a risk of infection or contamination of the substance and/or the syringe. This risk is considerably reduced with pre-filled syringes.

Typically syringes have a thin channel at the place where the needle is connected. In the case of glass syringes this thin channel is formed by use of a tungsten pin which serves as a forming tool during the forming process. The heated glass is pressed onto the exterior surface of the tungsten pin in the region of the channel. After completion of the forming process the tungsten pin is removed from the syringe and the channel remains.

Without the use of the tungsten pin the thin channel cannot be manufactured with the desired accuracy. In addition, there is a risk that the channel will be closed without the use of the tungsten pin during the forming process. Thus, the pin is made of tungsten because it is able to withstand the high temperatures to which the glass has to be brought during the forming process in order to achieve the required viscosity without substantial chemical or mechanical changes. Here, however, it is disadvantageous that abrasion occurs when the tungsten pin is removed so that tungsten residues remain within the syringe which can migrate into the stored substance. This is particularly undesirable when pharmaceutical substances are stored in the syringe.

In addition, syringes have relative complicated geometries in order to be able to connect cannulas or tubings for the application of the pharmaceutical substances. As an example, at this point a Luer-Lock connector may be mentioned, which can be manufactured only with considerable effort from glass and is not suitable for a mass production by use with glass. For these reasons there is a tendency to use pre-filled syringes made of plastic, whereby it is possible to produce even more complex geometries with relative little effort, for example by means of an injection molding process. However, the molding tools for manufacturing plastic syringes are relative complex, such that the production of plastic syringes is usually profitable only for large quantities. In addition, a separate molding tool must be provided for each syringe size. However, plastic materials have not nearly the same inert properties as glass, so that only a limited number of pharmaceutical substances can be stored in plastic syringes. In addition, the shelf life of pharmaceutical substances in plastic syringes is lower than that of glass syringes due to the lower diffusion resistance. Moreover, considerable permeation losses occur during storage. These permeation losses can be reduced by special coatings, which, however, are complicated to produce.

US 2010/0280414 A1 on the one hand discloses a container for storing a biological sample such as blood, which is closed with a plug-shaped connecting element, which is attached to the container exclusively via the lateral inner surface. Here, a frictional connection is provided. On the other hand US 2010/0280414 A1 discloses a container in which a needle holder interacts with the outer surface of a cylinder by means of a form-fit or frictional connection and is thus attached to the container.

DE 101 02 054 discloses a vial with a predetermined breaking point which can be closed with a plug, which, however can also be attached to the vial only via the inner surface of the container.

Both containers are not suitable for applying viscous substances, because the joint between the container and the corresponding connecting elements cannot bear the forces occurring thereby.

SUMMARY

Thus, it is an object of the present invention to improve the container of the aforementioned type for storing a substance such that on the one hand it has a high diffusion resistance and excellent inert properties, and on the other hand can be produced cost-efficiently even if the connecting element has a complex geometry.

According to the invention the plastic material is a thermoplastic or thermosetting plastic material and the glass body and the connecting element are connected to each other by use of a joint provided by a joining process, wherein said connecting element disposed at the distal end comprises a passage channel communicating with the first opening. A thermoplastic plastic material means plastic materials which can be deformed within a certain temperature range. For providing the joint a thermal joining process can be used, in which the thermoplastic plastic material is heated and deformed so that a bond with the glass body is provided. The glass itself is not deformed.

In the case of thermosetting plastic materials the connecting element may be formed in an injection molding tool, wherein a two-component system can be used which effects the curing of the thermosetting plastic material. For example, an epoxy resin can be used. In this joining process the bond with the glass body is formed during curing of the thermosetting plastic material. Again, the glass remains unchanged. Both joining processes have in common that they act only on the connecting element and the bond is provided by changing the viscosity of the entire connecting element or parts thereof. In addition, the shape of the connecting element is at least minimally changed during the joining process.

The container according to the invention combines the advantages of the glass, already stated above, in particular its inert properties and diffusion resistance, with the advantages of the plastic material, i.e. in particular the simplified shaping, so that the connecting elements can be provided even with complex geometries without large additional effort. Here, the glass body of the container according to the invention has a geometry which can be produced easily and makes up most of the area of contact with the stored substance. Compared to a container which is made entirely of glass the inert properties and the diffusion resistance of the container according to the invention do not decrease significantly, wherein the additional production expenditure is kept within narrow limits.

The temperatures required for shaping the thermoplastic or thermosetting plastic materials are well below those that are necessary for forming glass. This results in further advantages over pure glass containers. The energy demand for the manufacturing process is significantly lower compared to conventional glass syringes due to the lower temperatures. But even compared to plastic syringes the energy demand is reduced since the connecting elements are smaller compared to complete plastic syringes and thus less volume of plastic material has to be heated and formed, resulting in a saving of material, too.

Since the connecting elements are made of a plastic material no tungsten pin is required even for complex geometries, so that the container according to the invention does not have any tungsten residues which might adversely affect the stored substance. This in particularly applies to the passage channel which can be produced substantially easier with a connecting element which is made of plastic instead of glass. Tungsten pins are not required. Generally, it is preferred that the connecting element is made of a type of plastic material, however, it is also possible that the connecting element also comprise a plurality types of plastic materials or other materials such as metal, for example for reinforcing the connecting element.

The distal end should be understood as the end of the container facing away from the hand of the manipulating person during the application of the substance. During the application the substance passes through the first opening and the passage channel and thus may exit the cavity.

Herein, it is preferable that the joint is permanent. A permanent joint should be understood as a joint that in the intended use cannot be detached without damaging the joint itself, the glass body and/or the connecting element. However, a detachable joint can be realized, too, and to this end in particular a frictional connection is suited. However, the permanent joint is preferably used for connecting elements to which cannulas, tubings or similar components are connected. Due to the permanent configuration of the joint it is prevented that the joint is inadvertently detached, whereby the stored substance could leak out of the container and be lost.

In addition, the joint may be provided by use of a suitable adhesive in order to connect the connecting element made of plastic material with the glass body. The adhesive can also be used additionally in the abovementioned joining processes in order to reinforce the joint. Another alternative is a frictional connection between the connecting element and the glass body.

In a preferred development of the container the glass body has a proximal end with a second opening, wherein at the distal end a first connecting element and at the proximal end a second connecting element is connected to the glass body. Preferably, the glass body substantially has a hollow cylindrical shape and forms a distal end with a first opening and a proximal end with a second opening, wherein the openings are enclosed by end faces and by immediately adjacent surfaces of the glass body and the or each connecting element are connected to the glass body via the end faces and/or the immediately adjacent surfaces. In this development the glass body is configured as a substantially tubular glass body. The immediately adjacent surfaces in this case are preferably that portion of the inner surface of the glass body which adjoins the end face. If the glass body has a hollow cylindrical shape it can be manufactured inexpensively in a simple manner, for example, from a tubular glass. The tubular glass is essentially only cut to the appropriate length to provide the desired volume, without requiring any changes to the connecting elements. Consequently, only the length must be changed in order to change the volume of the cavity. Thus, for different volumes of the container no further tools for manufacturing the connecting elements are required and therefore the container according to the invention can flexibly and inexpensively be provided with the desired volumes. No additional processing steps with respect to the glass body itself are necessary. Only the connecting elements are provided with the geometry which is required for the respective use. In this way the containers can be manufactured particularly cost-efficiently and in different configurations, because a modular system consisting of various connecting elements can be realized, wherein the connecting elements can be connected to the tubular glass with a selectable length via a uniform interface.

Here, the glass body can consist of a glass layer or several glass layers. Multilayer glass bodies have the advantage that damages to the glass body do not directly result in a leak. Damages can be caused, for example, by mechanical, chemical or thermal impacts. Mechanical impacts can be, for example, forces or momentums exerted to the glass body by the user, thermal impacts are caused by temperature fluctuations in particular in the range of −20° C. to +40° C. Both types of impacts result in cracking. Chemical impacts may emanate from the stored substance and may, for example, result in delamination. By means of the multilayer structure crack propagation is prevented. If one layer is no longer sealing, the other layer seals the container.

When the connecting element is connected to the glass body not only via the end face, but also via the surfaces immediately adjacent thereto, the area of contact can be enlarged, which enables to provide a more stable joint. This is in particular advantageous for viscous substances in which a high pressure has to be exerted during the application, which the joint has to withstand.

Here, the first connecting element is preferably formed as a Luer-Lock connector. Luer-Lock connectors are widely used in laboratory, medical and pharmaceutical applications, for example, in order to connect tubings or cannulas to the distal end. A Luer-Lock connector is a standardized component which substantially comprises an internal thread with a standardized, relatively large pitch, and a coaxially extending cone. Since the Luer-Lock connector must be manufactured according to standards, high demands are placed on its production regarding the accuracy such that its production of glass is very expensive. The required precision is difficult to provide with glass such that there is a relative high rejection rate. In addition to the expensive production glass is not particularly suitable for use as a Luer-Lock connector because of its brittle material behavior. According to the invention a Luer-Lock connector can be produced of plastic material and can be connected to the hollow cylindrical glass container, such that on the one hand the production process can be simplified and on the other hand the Luer-Lock connector is able to bear much higher forces compared with glass due to the higher elasticity of the plastic material.

In a particularly preferred development of the container according to the invention the second connecting element is configured as a finger flange. In this development the container according to the invention is particularly suitable for syringes pre-fillable with a substance, wherein via the second opening at the proximal end at which the finger flange is disposed a piston can be inserted into the hollow cylindrical glass container. The piston is configured such that it seals the cavity against the respective proximal end such that no substance can escape at this end. At the distal end, for example, a Luer-Lock connector can be provided, into which appropriate closures can be screwed such that the container is also sealed at the distal end in order to prevent leakage of the substance from the cavity. After the Luer-Lock connector is opened a cannula can be connected such that the substance can be conveniently applied, to which end the user can push the piston into the cavity with his thumb, while his fingers are supported on the finger flange. The finger flange can also have a "backstop" function such that the piston cannot be inadvertently removed from the cavity. According to the invention such pre-fillable syringes can be manufactured in a simple way and cost-efficiently.

In a further embodiment of the container according to the invention a gasket is provided between the glass body and the connecting element, wherein the gasket is spaced apart from the joint. The gasket may be realized, for example, by an O-ring, which produces a certain frictional force between the connecting element and the glass body. In addition to the sealing effect the joint between the glass body and the connecting element is relieved. If, for example, the substance is pressed through the connecting element out of the cavity by means of a piston, a part of the forces thus acting on the connecting element is transferred via the gasket to the glass body, such that the joint does not have to absorb this part of the forces. Consequently, the probability of a failure of the joint can be reduced during use of the container according to the invention. In addition, by providing the gasket it can be avoided that the substance comes into contact with the joint. This makes it possible to use even adhesives that may otherwise diffuse into the substance. Such a diffusion is not acceptable in particular for pharmaceutical substances. However, adhesives can stabilize the joint such that in this embodiment the stabilizing effect of adhesives can be used without having to take into account the adverse diffusion.

Preferably, the thermoplastic plastic material is a cyclo-olefin copolymer (COC), a cyclo-olefin polymer (COP), acrylonitrile-butadiene-styrene (ABS), polyamide (PA), polylactate (PLA), polymethylmethacrylate (PMMA), polycarbonate (PC), polystyrene (PS) or polyethylene terephthalate (PET). The thermosetting plastic material is preferably a cellulose acetate (CA) or a transparent thermosetting resin.

In particular, the cyclo-olefin polymers and cyclo-olefin copolymers have a high diffusion resistance so that they are particularly suitable for the preparation of a Luer-Lock connector. Because pre-filled syringes already have a piston which is inserted into the cylindrical glass body, it is not necessary to additionally seal the glass body at this end. Consequently, the plastic material that is used for the finger flange is not required to have any particularly high diffusion resistance, such that other thermoplastic and thermosetting plastic materials are suitable for the preparation of the finger flange. Due to legal regulations the Luer-Lock connector must be transparent such that the substance is easily visible from outside. All of the mentioned plastic materials can be provided transparently. The finger flange on the other hand can also be provided with a color in order to assist the doctor or nurse in associating different syringes.

The plastic materials mentioned are sufficiently investigated so that the connecting element can be manufactured depending on the application from a respective suitable plastic material, which results in a wide variety of products with relative little effort.

Another aspect of the present invention relates to the use of a container according to any one of the previous exemplary embodiments for the storage and/or application of a pharmaceutical substance. A pharmaceutical substance should be understood as a drug which is used specifically for the treatment of a human or animal body. The advantages resulting from the use of a container according to any one of the aforementioned exemplary embodiments are in particular to be seen in that the glass element of the container according to the invention has not to be subjected to a hot forming process in order to produce a desired geometric shape of the glass body at certain points. In particular, no tungsten pin must be used to form thin channels. Consequently, the glass body according to the invention has no tungsten residues that could migrate into the stored substance. Furthermore, the connecting elements can be provided with complex geometries without great effort. In this respect, the container according to the invention is particularly suitable as a pharmaceutical primary packaging material such as pre-fillable syringes. In addition, pre-fillable syringes are particularly quick ready for use, because the substance does not have to be transferred from one container to another container. By eliminating the transfer process also the risk of infection and contamination is reduced, which is an essential advantage.

The invention is explained below in detail with reference to a preferred exemplary embodiment.

BRIEF DESCRIPTION OF THE DRAWINGS

The sole FIGURE shows a preferred embodiment of the container according to the invention in a sectional view.

DETAILED DESCRIPTION

The container 10 according to the invention shown in the FIGURE comprises a glass body 12 which in the illustrated exemplary embodiment has a hollow cylindrical shape with a distal end $14_1$ with a first opening $15_1$ and a proximal end $14_2$ with a second opening $15_2$. The glass body 12 encloses a cavity 16, in which a substance (not shown) such as a pharmaceutical substance can be stored. At each of the ends $14_1$, $14_2$ the glass body 12 has an end face 18, respectively. At the distal end $14_1$ a first connecting element $20_1$ and at the proximal end $14_2$ a second connecting element $20_2$ are respectively connected to the glass body 12 by means of a joint 22 provided by a joining process, wherein the joint 22 is arranged on the end faces 18 of the glass body 12. The connecting elements 20 are made of a thermoplastic or thermosetting plastic material or comprise these types of plastic materials, which enables the joint 22 with the glass body 12. The first connecting element $20_1$ arranged at the distal end $14_1$ has a passage channel 23 which is in communication with the first opening $15_1$ such that the substance can be delivered through the first opening $15_1$ and the passage 23 out of the cavity 16 to the outside of the container 10. Here, the passage channel 23 can selectively be closed in order to prevent an uncontrolled escape of the substance out of the cavity 16.

In the illustrated example the first connecting element $20_1$ is configured as a Luer-Lock connector 24, wherein the Luer-Lock connector 24 has a protrusion 26 which protrudes into the cavity 16 of the container 10. A gasket 28 is attached between the Luer-Lock connector 24 and the glass body 12 in order to seal the Luer-Lock connector 24 against the glass body 12 and thus the cavity 16 at the distal end $14_1$ and to support the joint 22 between the Luer-Lock connector 24 and the glass body 12. Herein, the gasket 28 cooperates with a surface 29 immediately adjacent to the end face 18, in this case, with the inner surface of the glass body 12.

At the proximal end $14_2$ the second connecting element $20_2$ is formed as a finger flange 30, which itself has an opening 32 having substantially the same cross-sectional shape and area as the second opening $15_2$ of the proximal end $14_2$. Through the opening 32 and the second opening $15_2$ of the proximal end $14_2$ a piston (not shown) can be inserted into the cavity 16. A gasket such as at the distal end $14_1$ is not necessary in this case since the piston itself seals against the glass body 12 so that the cavity 16 is also sealed against the proximal end $14_2$. The finger flange 30 may alternatively slightly project beyond the glass body 12 radially inwardly such that a backstop function is realized and the piston cannot be inadvertently removed from the cavity 16.

In the illustrated embodiment the container 10 is particularly suitable as a pre-fillable syringe such that a substance, in particular a pharmaceutical substance, can be introduced into the cavity 16 and stored therein by the manufacturer in the required quantity and can be transported and applied as needed. The substance can for example be applied by attaching a cannula to the Luer-Lock connector 24 by means of which the skin of a human or animal body to be treated can be punctured. By pushing the piston into the cavity 16 the substance is supplied into the body to be treated via the first opening $15_1$ of the distal end $14_1$, the passage channel 23 and the cannula. Here, the terms distal and proximal refer to the position of the syringe during the application of the substance into the patient's body from the perspective of the manipulating person. During the application the substance is supplied from the proximal end $14_2$ to the distal end $14_1$.

LIST OF REFERENCE NUMERALS 10 container
12 glass body
$14_1$ distal end
$14_2$ proximal end
$15_1$ first opening
$15_2$ second opening
16 cavity
18 end face
20, $20_1$, $20_2$ connecting element
22 joint
23 passage channel
24 Luer-Lock connector
26 protrusion
28 gasket
29 adjacent surface
30 finger flange
32 opening

What is claimed is:

1. A container for storing and/or applying a substance, comprising:
    a glass body having a substantially hollow cylindrical shape defining a cavity and having a first end with a first opening defined by a first end face and a first immediately adjacent surface; and
    a first connecting element, wherein the first connecting element comprises a plastic material,
    wherein the first connecting element comprises a Luer-Lock connector,
    wherein the first connecting element is directly attached by a first joint to the first end face and is further attached to the first immediately adjacent surface,
    wherein the first immediately adjacent surface is an internal surface,
    wherein the first connecting element has a maximum outer diameter that is smaller than or equal to the outer diameter of the glass body, and
    wherein the first joint is a permanent joint.

2. The container according to claim 1, wherein the first connecting element is a Luer-Lock connector.

3. The container according to claim 1, wherein the glass body further comprises a second end with a second opening defined by a second end face and a second immediately adjacent surface, a second connecting element attached to the glass body at the second end, the second connecting element comprising a thermoplastic or thermosetting plastic material, wherein the second connecting element is attached by a second joint to the second end face and is attached to the second immediately adjacent surface.

4. The container according to claim 3, wherein the first immediately adjacent surface is an internal surface of the cavity.

5. The container according to claim 4, wherein the first connecting element is attached to the first immediately adjacent surface by a gasket, the gasket being spaced apart from the first joint.

6. The container according to claim 3, wherein the first connecting element is a Luer-Lock connector.

7. The container according to claim 6, wherein the second connecting element is a finger flange.

8. The container according to claim 7, the finger flange projects radially inwardly of the second opening to define a piston backstop.

9. The container according to claim 1, wherein the plastic material further comprises a thermosetting plastic material.

10. The container according to claim 9, wherein the thermosetting plastic material is a cellulose acetate (CA) or a transparent thermosetting resin.

11. The container according to claim 1, wherein the glass body and the first connecting element are configured to store a pharmaceutical substance.

12. The container according to claim 1, wherein the glass body and the first connecting element are configured to apply a pharmaceutical substance.

13. The container according to claim 1, wherein the plastic material is a thermoplastic material.

14. The container according to claim 13, wherein the plastic material comprises a thermoplastic material selected from the group consisting of a cyclo-olefin copolymer (COC), a cyclo-olefin polymer (COP), acrylonitrile-butadiene-styrene (ABS), polyamide (PA), polylactate (PLA), polymethylmethacrylate (PMMA), polycarbonate (PC), and polyethylene terephthalate (PET).

15. A container for storing and/or applying a substance, comprising:

a glass body having a substantially hollow cylindrical shape defining a cavity and having a first end with a first opening defined by a first end face and a first immediately adjacent surface; and a first connecting element attached to the glass body at the first end, the first connecting element comprising a plastic material, wherein the first connecting element includes a first passage channel communicating with the first opening, and wherein the first connecting element is attached by a first joint to the first end face and also attached to the first immediately adjacent surface, wherein the first immediately adjacent surface is an internal surface, wherein the first joint is a permanent joint with a material bond, so that the first connecting element and the glass body cannot be detached without damaging at least one of the glass body, the first joint, and the connecting element.

16. A container for storing and/or applying a substance, comprising:

a glass body having a substantially hollow cylindrical shape defining a cavity and having a first end with a first opening defined by a first end face and a first immediately adjacent surface; and a first connecting element attached to the glass body at the first end, the first connecting element comprising a plastic material, wherein the first connecting element includes a first passage channel communicating with the first opening, and wherein the first connecting element is attached by a first joint to the first end face and is attached to the first immediately adjacent surface, wherein the first immediately adjacent surface is an internal surface, wherein the first connecting element does not radially exceed the glass body, and wherein the first joint is a permanent joint, so that the first connecting element and the glass body cannot be detached without damaging at least one of the glass body, the first joint, and the connecting element.

* * * * *